United States Patent [19]

Ulrich et al.

[11] 4,445,513
[45] May 1, 1984

[54] DEVICE FOR STRAIGHTENING SPINAL COLUMN

[75] Inventors: Bernhard Ulrich, Ulm, Fed. Rep. of Germany; Gys H. Slot, Nijmegen, Netherlands

[73] Assignee: Max Bernhard Ulrich, Ulm, Fed. Rep. of Germany

[21] Appl. No.: 383,169

[22] Filed: May 28, 1982

[30] Foreign Application Priority Data

May 29, 1981 [DE] Fed. Rep. of Germany ....... 3121271

[51] Int. Cl.³ .............................................. A61F 5/00
[52] U.S. Cl. .................................. 128/69; 128/92 R; 128/92 B; 128/92 E
[58] Field of Search ...................... 128/69, 92 R, 92 B, 128/92 E, 75, 78

[56] References Cited

U.S. PATENT DOCUMENTS

| | | | |
|---|---|---|---|
| 2,774,350 | 12/1956 | Cleveland, Jr. ................... | 128/92 R |
| 3,242,922 | 3/1966 | Thomas ............................ | 128/92 R |
| 3,997,138 | 12/1976 | Crock et al. .................... | 128/92 B X |
| 4,289,123 | 9/1981 | Dunn ............................... | 128/92 B X |

FOREIGN PATENT DOCUMENTS

| | | | |
|---|---|---|---|
| 2649042 | 9/1978 | Fed. Rep. of Germany ........ | 128/69 |
| 485739 | 12/1975 | U.S.S.R. ................................ | 128/69 |

*Primary Examiner*—Ronald L. Frinks
*Attorney, Agent, or Firm*—Karl F. Ross; Herbert Dubno

[57] ABSTRACT

A device for straightening a spinal column having a succession of vertebrae extending along a nonstraight line lying generally in a plane has an elongated bar lying generally in the plane of the line and having a pair of relatively longitudinally displaceable bar parts in turn having respective bar ends. A pair of connectors of the bar ends are secured to respective vertebrae of the succession. Respective pivots between the connectors and the respective ends define therebetween respective generally parallel axes transverse to the plane. A main abutment movable along and flexible on one of the parts and longitudinally engageable with the other of the parts serves for limiting relative longitudinal displacement of the parts toward each other. Thus the main abutment can be moved along the one part to increase the spacing between the ends and thereby can straighten the succession of vertebrae between the connectors.

12 Claims, 5 Drawing Figures

DEVICE FOR STRAIGHTENING SPINAL COLUMN

FIELD OF THE INVENTION

The present invention relates to a device for straightening a spinal column having a succession of vertebra lying in a nonstraight line. More particularly this invention relates to an orthopedic surgical tool for straightening and splinting a spinal column deformed by lordosis, kyphosis, or scoliosis.

BACKGROUND OF THE INVENTION

Curvature of the spine, whether dorsally convex from kyphosis, forwardly or ventrally convex from scoliosis, or laterally curved from lordosis, can be corrected by an orthopedic surgical technique of simply forcing the curved succession of vertebrae into a straight position and then holding them forcibly in this position. When the ligaments readjust the splinting holding the vetebrae in the new position can be removed and these vertebrae will normally remain in the newly set position.

U.S. Pat. Nos. 2,774,350 of C.S. Cleveland describes an arrangement wherein the spinal processes of the vertebrae being straightened are exposed in a long surgical incision and are secured to respective clips carried on respective threaded rods. The other ends of these rods pass through guides slidable along a main threaded rod lying in the plane of the spinal curvature. The clip-carrying rods have nuts flanking the respective guides so the distance from the main rod to each clip can be changed and set. The distance between adjacent guides on the main rod can be adjusted similarly by means of pairs of nuts flanking the guides. Thus the vertebrae can be pulled into a straight line by shortening the distance between the main rod and the middle clips and simultaneously increasing the distance between guides along the main rod.

Such as arrangement is quite bulky and takes enormous pains to operate, as the surgeon must tighten the various nuts one at a time and only a slight increment each time to create the desired shape, so that the straightening operation is extremely laborious. After the spine is straightened, the entire device must be left projecting through the long incision until the new position has set, that is until the ligaments that hitherto were on the inside of the curve have stretched and those on the outside of the curve have shrunk to their new equal sizes. Obviously these disadvantages make this device less than wholly satisfactory for the surgeon and patient.

It is also known from German Pat. No. 2,649,042 based on an application filed Oct. 28, 1976 by M. B. Ulrich to provide an implantable splint that constitutes part of the device that actually does the straightening, and that can be left in the patient after the spine is straightened to keep the hitherto curved portion of the spine straight, although it is noted of course that the term "straight" is relative only as virtually all parts of the spine are at least gently curved. This splint has a threaded rod that is bendable and extends through a succession of anchors secured to the vertebrae to be straightened. Another implement is employed to initially straighten the succession of vertebrae, with concomitant adjustment of pairs of nuts on the threaded rod that flank the respective anchors. Once the desired straightness is established, the pairs of nuts are tightened against the respective anchors to lock in the set position. This system allows the patient to be closed up after surgery, but still entails considerable work for the initial straightening operation. In addition the rod or rods, which must be flexible in order to follow the original curved line of the anchors, cannot be very rigid, so that occasionally the spine will at least partially revert to its initial nonstraight position.

It is also known to use so-called distraction rods or bars to straighten curved portions of the spine and subsequently to splint the straightened portion in position. Such rods have hooks on their ends that engage over lateral sides of the bony processes of the vertebrae. Normally they are secured in place once the appropriate portion of the spine has been straightened, and are left implanted. Such devices have the disadvantage that they rarely match the exact anatomical shape. In addition, when made adjustable they occasionally come disconnected, requiring corrective surgery to reconnect them.

OBJECTS OF THE INVENTION

It is therefore an object of the present invention to provide an improved device for straightening and splinting a spinal column.

Another object is the provision of such a device for straightening and splinting a spinal column which overcomes the above-given disadvantages.

A further object is to provide such a device which allows the surgeon to rapidly and easily effect the required straightening, which term is here used to cover any lessening of curvature.

Yet another object is to provide such a device which has simple and rigid splints that can be implanted and that will surely hold the straightened spine portion in the desired shape.

SUMMARY OF THE INVENTION

These objects are attained according to the instant invention in a device for straightening a spinal column having a succession of vertebrae extending along a nonstraight line lying generally in a plane. This device has an elongated bar lying generally in the plane of the line and having a pair of relatively longitudinally displaceable bar parts in turn having respective bar ends. A pair of connectors at the bar ends are secured to respective vertebrae of the succession. Respective pivots between the connectors and the respective ends define therebetween respective generally parallel axes transverse to the plane. Means including a main abutment movable along and fixable on one of the parts and longitudinally engageable with the other of the parts serves for limiting relative longitudinal displacement of the parts toward each other. Thus the main abutment can be moved along the one part to increase the spacing between the ends and thereby can straighten the succession of vertebrae between the connectors.

This arrangement can therefore be used relatively easily to establish the desired spacing between the two outermost vertebrae of the succession. Due to the pivotal connection it is possible to exert a considerable straightening force on these outer vertebrae without damage to them. Furthermore the straightening force can be exactly and easily dosed. Nonetheless the straightening can be carried out rapidly.

The device according to the invention further has end parts which each have two generally perpendicular flanges one of which is provided with projecting points and is shaped to fit onto a vertebra end surface with the points engaged therein and the other of which is shaped to fit simultaneously onto a vertebra side surface and is provided with the respective pivot. In this manner the ends are solidly mounted to these vertebrae so that considerable force can be brought to bear without breaking them out. Normally according to this invention each of the other flanges is provided with at least one tab carrying an axle pin constituting the respective pivot and traversing the respective end. These axle pins are generally parallel to the respective other flanges. Such end parts therefore sit very solidly on the respective vertebrae.

According to another feature of the instant invention one of the parts is a rod and the other a tube, and they telescope together. The main abutment is carried on the rod and is engageable with the tube. More specifically the rod is threaded and the main abutment is a nut threaded on the rod. Such a system makes it very simple to control the straightening force finely and steplessly.

In such a device the tube is formed to one side of the main abutment with a secondary abutment directed toward the main abutment and the rod is formed to the other side of the main abutment with another secondary abutment. It is possible to adjust the length of such a device by means of a plier-type spreader tool engageable with the secondary abutments and actuatable to push same apart. Thus the pliers longitudinally separate the tube and rod, whereupon the nut is screwed along to lock in the set spacing, and so on.

It is also possible according to this invention for the bar to have at least one generally cylindrical extremity and for the respective end to be fitted therein for rotation about the longitudinal axis of the bar. More specifically the end part of the cylindrical extremity includes a filler part having a socket fitted over the extremity and a cylindrical extremity identical to that of the bar, and a pivot part connected to the respective pivot and having a socket fitted over the extremity of the filler part. With this system the distractor/straightener can be spread as described above with the pliers until it is at the limit of its extensibility. Then the ends are propped apart temporarily, the main abutment is screwed back down the rod so that the one extremity can pull out of the filler part, and another filler part is fitted in. Virtually any reasonable length can be constructed in this manner. In addition the use of the plier-type spreader plus the easy to rotate main abutment makes such a procedure quite easy and rapid.

The invention also comprises a splint having two anchors securable to side surfaces of respective vertebrae of the succession and a rigid spacer rod having opposite ends secured in the anchors and extending straightly therebetween. According to this invention the anchors are screws having heads forming seats for the opposite ends.

DESCRIPTION OF THE DRAWING

The above and other features and advantages will become more readily apparent from the following, reference being made to the accompanying drawing in which.

SPECIFIC DESCRIPTION

Figure 1:
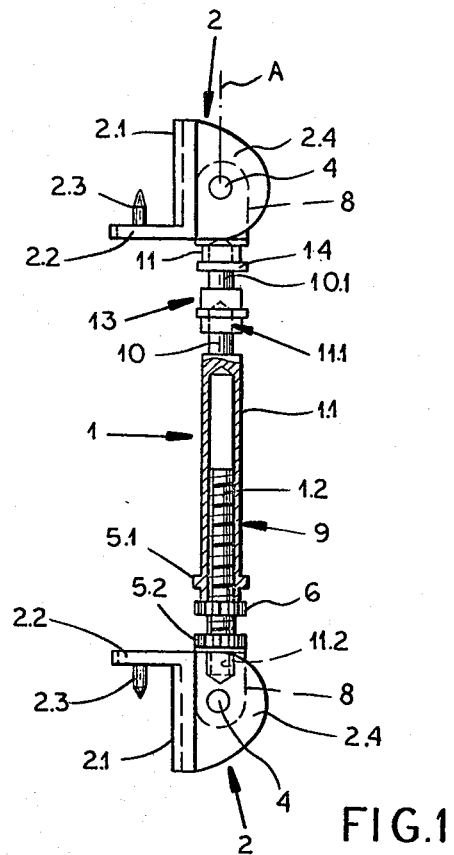
FIG. 1 is a side view partly in axial section through a straightening device according to this invention.
Figure 2:
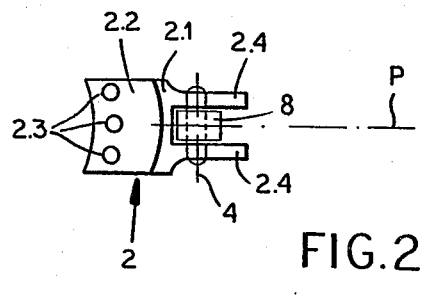
FIG. 2 is a top view of the device of FIG. 1.
Figure 3:
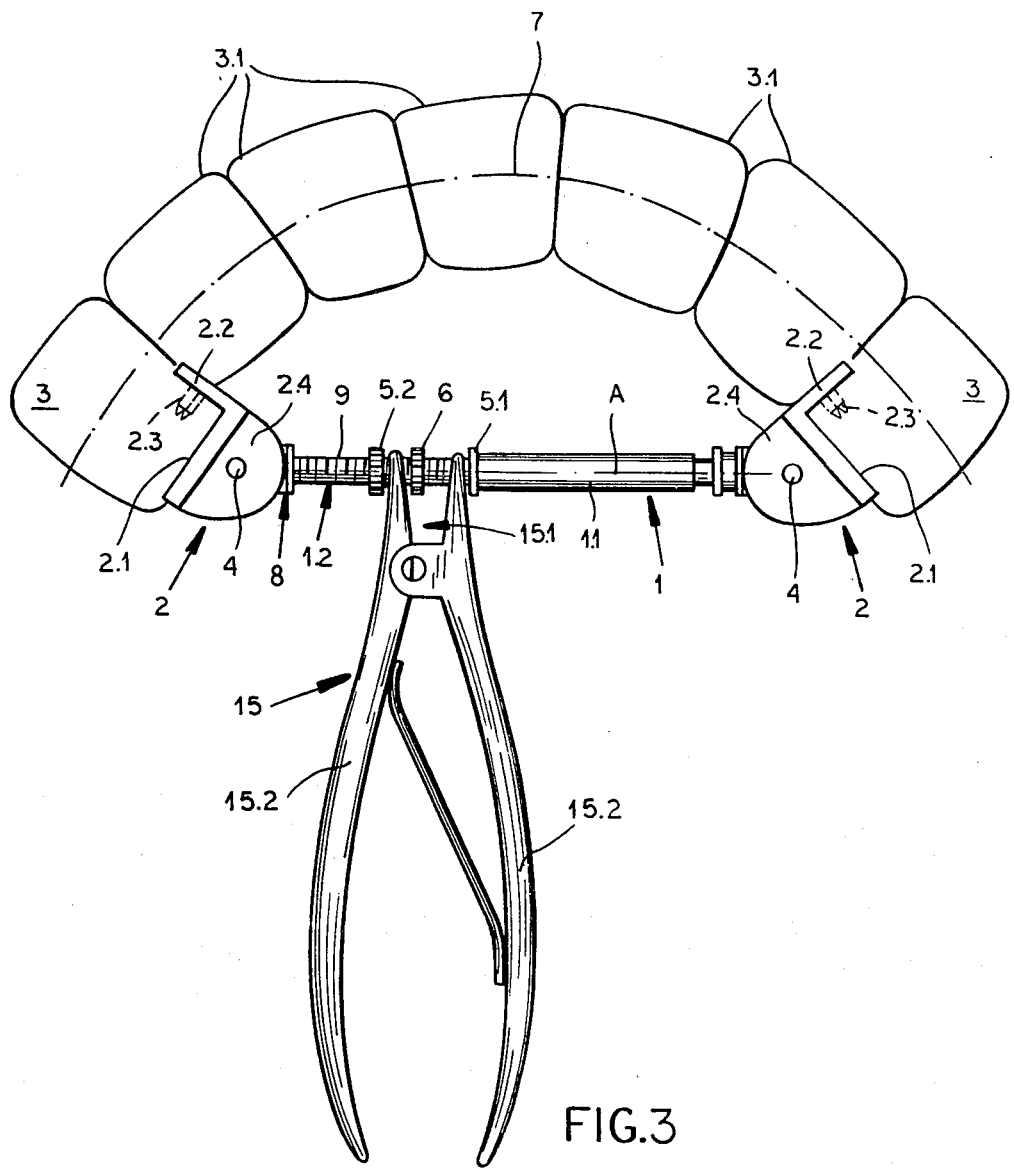
FIG. 3 is a side view illustrating use of the device according to this invention.

As seen in FIGS. 1–3 the device according to this invention basically comprise a distraction bar 1 having connectors 2 that are attached to the end vertebrae 3 of a succession of vertebrae 3, 3.1 extending along a curved line 7 defining a plane P (FIG. 2 only) on which the bar 1 lies and which in FIGS. 1 and 3 is the plane of the drawing. The ends of the bar are connected to the connectors 2 by parallel pivot pins 4 perpendicular to the plane P.

The bar 1 is formed of a tube 1.1 and a rod 1.2 telescoping in this tube 1.1 and formed with a screwthread 9. The cross section of the passage of the tube 1.1 and that of the rod 1.2 can be nonround and complementary to prevent the two from rotating relative to each other. Simply making the two parts cylindrical with a flat along one side of the rod 1.2 and a corresponding indent in the tube would be sufficient to rotationally link the two together. The tube 1.1 is formed adjacents its one end with an annular ridge or abutment 5.1. A ring 5.2 is threaded on the rod 1.2 adjacent this abutment 5.1, and another ring 6 is threaded on the rod 1.2 between the two abutments 5.1 and 5.2.

Each connector has a flange 2.1 that lies on the side surface of the respective vertebra and another flange 2.2 perpendicular thereto and provided with points or spikes 2.3 that can poke into the end surface of a vertebra 3 against which the flange 2.2 lies. The side flange 2.1 is formed with two cheeks or tabs 2.4 between which the respective axle pin 4 is fixed and extends. Eyes 8 on the ends of the bar 1 are traversed by these pins 4.

The upper end of the bar 1 is formed with a cylindrical projection or extremity 10 that fits in a socket or seat 11.1 of a filler part 13 that in turn has a cylindrical projection or extremity 10.1 identical to the extremity 10. This extremity 10.1 fits in a socket 11 formed on the eye 8, which socket 11 is identical to the socket 11.1. The filler 13 and eye 8 are formed with annular abutment rings or ridges 14 spaced apart along the axis A of the bar 1.

In use as seen in FIG. 3 the flanges 2.2 are fitted to the upper and lower vertebrae 3, with the flanges 2.1 lying on the side surface at the inside of the curve to be corrected. The tabs 2.4 are coplanar and normally the eyes 8 are carried right on the connectors 2 with the bar 1 separate.

This bar 1 is then installed with the abutment ring 5.1 and ring 6 screwed virtually to the end of the rod 1.2, and enough fillers or spacers 13 to fill the distance between the two eyes 8. The extremity 10 or 10.1 is fitted to the appropriate socket 11 or 11.1 and the end of the rod 9 is similarly aligned with the corresponding hole 11.2 of the lower eye 8. The abutment ring 6 is then screwed out until it is snug against the end of the tube 1.1 and the entire bar 1 is stiff between the connectors 2, and the other abutment ring 5.2 is drawn up near but not against the ring 6.

Then as shown in FIG. 3 a pliers tool 15 having a pair of jaws 15.1 and a pair of handles 15.2 is fitted to the bar 1, with the jaws 15.1 bearing on the confronting faces of the abutment 5.1 and 5.2. The surgeon squeezes the handles 15.2 together to force the abutments apart and lengthen the bar 1. Before releasing pressure on the handles 15.2 the abutment 6 is screwed along the screwthread 9 to lock in the set position. The other abutment 5.2 is then moved up toward the abutment 5.1 and the procedure is repeated.

At any time the entire assembly can be temporarily braced while the rings 5.2 and 6 are screwed back down the rod 1.2 and a filler 13 is inserted, to increase the overall length an increment. Thereafter the adjustment operation described above is repeated.

Figure 5:
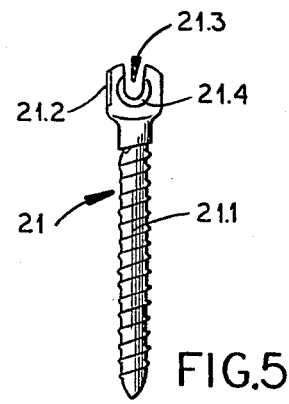
FIG. 5 is a side view of a detail of the splint of FIG. 4.
Figure 4:
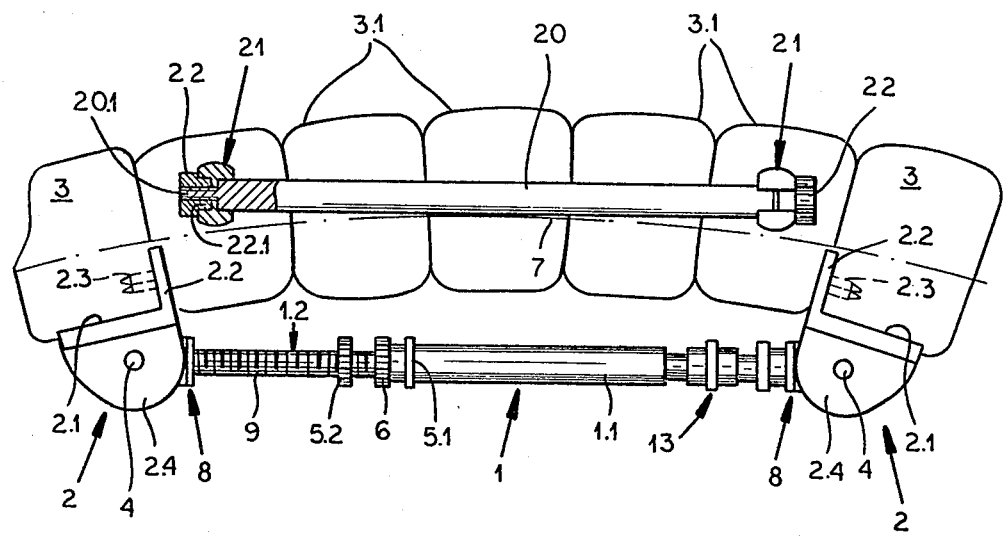
FIG. 4 is a view like FIG. 3 but showing the device after the spine portion has been straightened and splints have been mounted in place.

When as seen in FIG. 4 the succession of vertebrae 3, 3.1 is straightened, with the line 7 much straighter than in FIG. 3, implant splints are installed which each comprises a rod 20 and a pair of anchors 21. These anchors 21 are formed as seen in FIG. 5 like self-tapping screws, each having a threaded shank 21.1 and a head 21.2 formed with a notch 23.3 having a recessed seat 21.4. The rod 20 has small-diameter threaded ends 20.1 that are threaded into nuts 22 each having a collar 22.1 received in the respective seat recess 21.4.

The anchors are screwed into the spongy bone of the vertebrae 3.1 immediately adjacent those to which the connectors 2 are secured. Then a rod 20 of appropriate length is fitted to the anchors 21 and locked in place with the nuts 22. These rods 20, one of which may be applied to each side of the spinal column, are extremely rigid and will effectively inhibit the spine from returning to the shape it had before distraction.

Once the splints 20-22 are in place the bar 1 is shortened and removed and the connectors 2 are pulled loose and also removed. The incision can be closed.

The system according to the instant invention therefore is quite simple, but will allow the surgeon to rapidly and easily straighten a spine by distraction and then splint it. The equipment is simple and foolproof, easily handled by any orthopedic surgeon familiar with modern procedures.

We claim:

1. A device for straightening a spinal column having a succession of vertebrae extending along a nonstraight line lying generally in a plane, said device comprising:
    an elongated bar lying generally in said plane of said line and having a pair of relatively longitudinally displaceable bar parts in turn having respective bar ends;
    a pair of connectors at said ends and each having two generally penpendicular flanges one of which is provided with projecting points and is shaped to fit onto a vertebra end surface with said points engaged therein and the other of which is shaped to fit simultaneously onto a vertebra side surface and is provided with the respective pivot;
    means for securing said connectors to respective vertebrae of said succession;
    respective pivots between said connectors and the respective ends and defining therebetween respective generally parallel axes transverse to said plane; and
    means including a main abutment movable along and fixable on one of said parts and longitudinally engageable with the other of said parts for limiting relative longitudinal displacement of said parts toward each other, whereby said main abutment can be moved along said one part to increase the spacing between said ends and thereby can straighten the succession of vertebrae between said connectors.

2. The device defined in claim 1 wherein each of said other flanges is provided with at least one tab carrying an axle pin constituting the respective pivot and traversing the respective end.

3. The device defined in claim 4 wherein said axle pins are generally parallel to the respective other flanges.

4. The device defined in claim 1 wherein said parts telescope in each other, one being a rod and the other a tube.

5. The device defined in claim 4 wherein said main abutment is carried on said rod and engageable with said tube.

6. The device defined in claim 5 wherein said rod is threaded and said main abutment is a nut threaded on said rod.

7. The device defined in claim 1 wherein said parts telescope and include a threaded rod and a tube, said main abutment being a nut threaded on said rod and engageable longitudinally with said tube, said tube being formed to one side of said main abutment with a secondary abutment directed toward said main abutment and said rod being formed to the other side of said main abutment with another secondary abutment, said device further comprising a plier-type spreader tool engageable with said secondary abutments and actuatable to push same apart, whereby said main abutment can be screwed down to a new position against said tube.

8. A device for straightening a spinal column having a succession of vertebrae extending along a nonstraight line lying generally in a plane, said device comprising:
    an elongated bar lying generally in said plane of said line and having a pair of relatively longitudinally displaceable bar parts in turn having respective bar ends, said bar further having at least one generally cylindrical extremity, the respective end being fitted thereinto for rotation about the longitudinl bar axis, said end part of said cylindrical extremity including
        a filler part having a socket fitted over said extremity and a cylindrical extremity identical to that of said bar, and
        a pivot part connected to the respective pivot and having a socket fitted over the extremity of said filler part;
    a pair of connectors at said ends;
    means for securing said connectors to respective vertebrae of said succession;
    respective pivots between said connectors and the respective ends and defining therebetween respective generally parallel axes transverse to said plane; and
    means including a main abutment movable along and fixable on one of said parts and longitudinally engageable with the other of said parts for limiting relative longitudinal displacement of said parts toward each other, whereby said main abutment can be moved along said one part to increase the spacing between said ends and thereby can straighten the succession of vertebrae between said connectors.

9. A device for straightening a spinal column having a succession of vertebrae extending along a nonstraight line lying generally in a plane, said device comprising:
    an elongated bar lying generally in said plane of said line and having a threaded rod and a tube telescoped and longitudinally displaceable thereon, the rod and tube having respective bar ends;

a pair of connectors at said ends;

means for securing said connectors to respective vertebrae of said succession;

respective pivots between said connectors and the respective ends and defining therebetween respective generally parallel axes transverse to said plane;

means including a main-abutment nut threaded on and movable along said rod and longitudinally engageable with said tube for limiting relative longitudinal displacement of said tube and rod toward each other, said tube being formed to one side of said nut with a secondary abutment directed toward said nut and said rod being formed to the other side of said nut with another secondary abutment, whereby said main abutment can be moved along said rod to increase the spacing between said ends and thereby can straighten the succession of vertebrae between said connectors; and a plier-type spreader tool engageable with said secondary abutments and actuatable to push same apart, whereby said nut can be screwed down to a new position against said tube.

10. The device defined in claim 9 wherein said bar has at least one generally cylindrical extremity and the respective end is fitted thereof for rotation about the longitudinal axis of the bar.

11. The device defined in claim 9, further comprising:
two anchors securable to side surfaces respective vertebrae of said succession; and a rigid spacer rod having opposite ends secured in said anchors and extending straightly therebetween.

12. The device defined in claim 11 wherein said anchors are screws having heads forming seats for said opposite ends.

* * * * *